US006628747B1

(12) United States Patent
Schotland et al.

(10) Patent No.: US 6,628,747 B1
(45) Date of Patent: Sep. 30, 2003

(54) SYSTEM AND METHOD FOR DUAL-BEAM INTERNAL REFLECTION TOMOGRAPHY

(75) Inventors: John Carl Schotland, Ladue, MO (US); Vadim Arkadievich Markel, Olivette, MO (US); Paul Scott Carney, Champaign, IL (US)

(73) Assignee: Washington University in St. Louis, St. Louis, MO (US)

( * ) Notice: Subject to any disclaimer, the term of this patent is extended or adjusted under 35 U.S.C. 154(b) by 9 days.

(21) Appl. No.: 10/177,429

(22) Filed: Jun. 21, 2002

(51) Int. Cl.[7] ............................ G21K 7/00; A61B 6/03; G01B 9/02

(52) U.S. Cl. ............................... 378/43; 378/4; 378/62; 356/496

(58) Field of Search ................................ 378/4, 43, 62, 378/901; 356/496, 511

(56) References Cited

U.S. PATENT DOCUMENTS 5,001,737 A * 3/1991 Lewis et al. ................ 378/147
2002/0021451 A1 * 2/2002 Hill ............................ 356/511
2003/0020920 A1 * 1/2003 Dave et al. ................. 356/479

OTHER PUBLICATIONS

Schotland and Carney, "Inverse Scattering for Near–field Microscopy", Applied Physics Letters, vol. 77, No. 18, pp. 2798–2800, Oct. 30, 2000.

Magerle, "Nanotomography", Physics Review Letter, vol. 85, No. 13, pp. 2749–2752, Sep. 25, 2000.

Carney, "The Optical Cross–secion Theorem with Incident Fields Containing Evanescent Components", Journal of Modern Optics, vol. 46, No. 5, pp. 891–899, 1999.

* cited by examiner

*Primary Examiner*—David V. Bruce

(57) ABSTRACT

A methodology and concomitant system for three-dimensional near-field microscopy achieves subwavelength resolution of an object without retrieval of the optical phase. The features of this approach are three-fold: (i) the near-field phase problem is circumvented by employing measurements of the power extinguished from probe fields; (ii) the fields on which the power measurements are performed may be monitored far from the object and thus subwavelength resolution is obtained from far zone measurements; and (iii) by developing an analytic approach to the inverse problem in the form of an explicit inversion formula, an image reconstruction algorithm is produced which is strikingly robust in the presence of noise.

11 Claims, 4 Drawing Sheets

SYSTEM AND METHOD FOR DUAL-BEAM INTERNAL REFLECTION TOMOGRAPHY

BACKGROUND OF THE DISCLOSURE

1.) Field of the Invention

This invention relates to tomography and, more particularly, to near-field tomography wherein an image of an object is directly reconstructed with sub-wavelength resolution using only amplitude measurements.

2.) Description of the Background Art

There has been considerable recent interest in the development of methods which extend the spatial resolution of optical microscopy beyond the classical diffraction limit. Researches in near-field optics have provided a powerful set of approaches to directly address this problem. These approaches, which include near-field scanning optical microscopy (NSOM) and total internal reflection microscopy (TIRM), have been used to obtain subwavelength-resolved maps of the optical intensity near surfaces of effectively two-dimensional systems. However, when the sample presents a manifestly three-dimensional structure, interpretation of the resultant images has proven to be problematic. Recently, significant progress towards the development of three-dimensional near-field imaging has been made on two fronts. Nanotomography, a destructive method in which a sample is successively eroded and then imaged layer by layer with a scanning probe microscope, was reported in the article entitled "Nanotomography" by R. Magerle, Physical Review Letters, Vol. 85, No. 13, pgs. 2749–2752, Sep. 25, 2000. A nondestructive approach has also been devised and is based upon the solution to the linearized near-field inverse scattering problem for three-dimensional inhomogeneous media; this approach, entitled "Inverse Scattering for Near-field Microscopy", was reported by P. S. Carney and J. C. Schotland, Applied Physics Letters, Vol. 77, No. 18, pgs. 2798–2800, Oct. 30, 2000. For this latter method, the input data for the image reconstruction algorithm depends on the amplitude and phase of the scattered field. Measurements of the optical phase, particularly in the near field, are notoriously difficult since detectors generally record only intensities, necessitating the use of a holographic measurement scheme.

Thus, the art is devoid of a three-dimensional near-field microscopy technique which achieves subwavelength resolution without retrieval of the optical phase.

SUMMARY OF THE INVENTION

These shortcomings, as well as other limitations and deficiencies, are obviated in accordance with the present invention, referred to as as "dual-beam internal reflection tomography", by illuminating an object with an incident field composed of a coherent superposition of incoming evanescent waves, and by providing a direct reconstruction technique to an inverse scattering problem using measurements of output waves detected with and without the presence of the object. The superoscillatory properties of such waves may be used to encode the structure of the object on subwavelength scales.

In accordance with a broad method aspect of the present invention, a method for generating a tomographic image of an object includes: (a) probing the object with incident waves composed of a superposition of evanescent waves; (b) detecting the power extinguished from the incident waves by the object; and (c) reconstructing the tomographic image by executing a prescribed mathematical algorithm with reference to the incident waves and the extinguished power to generate the tomographic image with subwavelength resolution.

A broad system aspect of the present invention is commensurate with the broad method aspect.

The features of this approach are three-fold: (i) the near-field phase problem is circumvented by employing measurements of the power extinguished from the probe fields; (ii) the fields on which the power measurements are performed may be monitored far from the object and thus subwavelength resolution is obtained from far zone measurements; and (iii) by developing an analytic approach to the inverse problem in the form of an explicit inversion formula, an image reconstruction algorithm is produced which is strikingly robust in the presence of noise.

DETAILED DESCRIPTION

Figure 1:
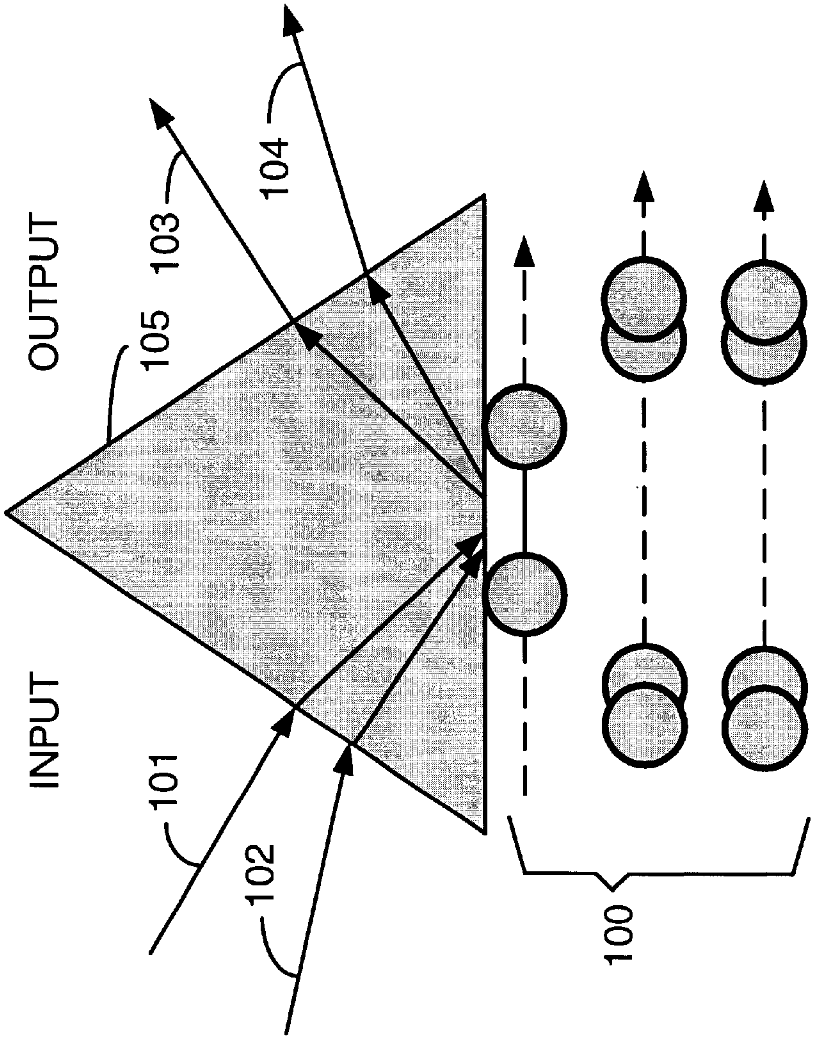
FIG. 1 illustrates a object/scatterer under test showing two input evanescent waves which are incident on the scatterer through a prism, and the extinguished power manifested by two output waves.

Begin by considering a monochromatic field incident on a dielectric medium with susceptibility or scattering potential $\eta(r)$. For simplicity, the effects of polarization are ignored and consider the case of a scalar field U(r) which obeys the reduced wave equation $$\nabla^2 U(r)+k_0^2 U(r)=-4\pi k_0^2\eta(r)U(r). \tag{1}$$

where $k_0$ is the free space wave number. The incident field will be taken to be composed of a superposition of two evanescent waves, as illustrated with reference to FIG. 1:

$$U^{(i)}(r)=a_1 e^{ik_1\cdot r}+a_2 e^{ik_2\cdot r}, \tag{2}$$

with amplitudes $a_3$ and $a_2$. Here the complex wavevectors $k_1$ and $k_2$ are of the form $k_j=(q_j,k_z(q_j))$ with transverse part $q_j$ and $k_z(q_j)=i(q_j^2-k_0^2)^{1/2}$ for j=1, 2. When the evanescent waves are generated by prism 105 of FIG. 1 having refractive index n, then $k_0\leqq|q_j\leqq nk_0$. By monitoring the change in the power content of the totally reflected waves due to the presence of the scatterer, one obtains the power lost by the probe fields, that is, the extinguished power. In a sense, the interference of these waves leads to a form of holography carried out within the scattering medium. In particular, incoming light beams 101 and 102 generate evanescent waves which are incident on the scatterer/object 100 through prism 105. The extinguished power is then measured, as manifested by output waves 103 and 104, at the output via difference measurements with and without the scatterer present. The power extinguished from the incident beams may be obtained from a generalization of the optical theorem expressed in the article entitled "The Optical Cross-section Theorem with Incident Fields Containing Evanescent Components" by P. S. Carney, Journal of Modern Optics, Vol. 46, No. 5, pgs. 891–899, 1999, and is given by the expression $$P(a_1,a_2)=\frac{4\pi}{k_0}\mathrm{Im}(|a_1|^2A(k_1^*,k_1)+a_1^*a_2A(k_1^*,k_2)+a_2^*a_1A(k_2^*,k_1)+|a_2|^2A(k_2^*,k_2)),\quad(3)$$

where $A(k_1,k_2)$ is the scattering amplitude associated with the scattering of a plane wave with wavevector $k_1$ into a plane wave with wavevector $k_2$. It will prove useful to extract the cross-terms from equation (3), that is, to gain information about the scattering amplitude for non-zero momentum transfer. This can be accomplished for any set of $k_1$ and $k_2$ through four measurements of the extinguished power where the relative phases are varied between measurements. To this end define the following data function, also known as scattering data:

$$D(k_1,k_2)=\frac{k_0}{8\pi a_1^*a_2}[P(a_1,ia_2)-P(a_1,-ia_2)+i(P(a_1,a_2)-P(a_1,-a_2))].\quad(4)$$

It may be seen from equation (3) that the data function is related to the scattering amplitude by $$D(k_1,k_2)=A(k^*_1,k_2)-A^*(k_2,k^*_1).\quad(5)$$

The data function uniquely determines $\eta(r)$ as may be seen from the analytic properties of the scattering amplitude. It should be stressed that this result is independent of any approximations beyond the use of a scalar model.

The inverse problem is now considered. The weak-scattering approximation is utlized, which is particularly suitable for the investigation of subwavelength structures. Accordingly, the scattering amplitude may be calculated perturbatively to lowest order in 77 with the result $$A(k_1,k_2)=k_0^2\int d^3re^{-i(k_1-k_2)\cdot r}\eta(r).\quad(6)$$

Noting that the wavevectors $k_1$ and $k_2$ may be specified by their transverse parts alone, it may be found that $$D(q_1,q_2)=2ik_0^2\int d^3r\exp[-i(q_1-q_2)\cdot\rho-i(k^*_z(q_1)-k_z(q_2))z]\alpha(r),\quad(7)$$

where $r=(\rho,z)$ with $\rho$ the transverse spatial coordinate, $\alpha(r)\equiv\mathrm{Im}\,\eta(r)$ is the absorptive part of the susceptibility, and the dependence of D on $q_1$ and $q_2$ has been made explicit.

Assume that $D(q_1,q_2)$ is known for $(q_1,q_2)$ in the data set Q and introduce a function $\chi(q_1,q2)$ which is unity if $(q_1,q_2)\in Q$ and is zero otherwise. For convenience, introduce the function $\Phi(q,Q)=D(q,Q+q)\chi(q,Q+q)/2ik_0^2$ where q, Q range over all space. Making use of these definitions, the following system of equations obtains:

$$\Phi(q,Q)=\int_0^L dzK(q,z;Q)\tilde{\alpha}(Q,z),\quad(8)$$

where $$K(q,z;Q)=\exp[i(k_z(Q+q)-k^*_z(q))z]\chi(q,Q+q),\quad(9)$$

$\alpha(Q,z)=\int d^2\rho\exp(iQ\cdot\rho)\alpha(r)$, and L is the range of $\alpha(r)$ in the z direction. For fixed Q, equation (8) defines a one-dimensional integral equation for $\alpha(Q,z)$ whose pseudoinverse solution has the form $$\alpha(Q,z)=\int d^2qd^2q'K^*(q,z;Q)\langle q|M^{-1}(Q)|q'\rangle\Phi(q',Q),\quad(10)$$

where the matrix element $\langle q|M^{-1}(Q)|q'\rangle$ is obtained from the overlap integral $$\langle q|M(Q)|q'\rangle=\int_0^L dzK(q,z;Q)K^*(q',z;Q).\quad(11)$$

It may be verified by direct substitution that equation (10) satisfies equation (8). Finally, apply the inverse Fourier transform in the transverse direction and note that the integrations may be restricted over Q to $|Q|<2nk_0$ and q, q' to $Q_1$ with $Q_{1=\{q1}:(q_1,q_2)\in Q\}$ to arrive at the main result:

$$\alpha(r)=\frac{1}{2i(2\pi)^2k_0^2}\int_{|Q|\le 2nk_0}d^2Qe^{-iQ\cdot\rho}\int_{Q_1\times Q_1}d^2qd^2q'\times K^*(q,z;Q)\langle q|M^{-1}(Q)|q'\rangle\chi(q',Q+q')D(q',Q+q')\quad(12)$$

which is the required inversion formula.

The solution constructed to the inverse problem is the unique minimum $L^2$ norm solution of equation (7). This statement follows from the fact that equation (12) may be interpreted as the singular value decomposition (SVD) of the pseudoinverse solution to equation (7). It is important to appreciate that the SVD provides a natural means of regularization of the inverse problem which sets the resolution of the reconstructed image to be commensurate with the available data. In particular, regularize $M^{-1}(Q)$ by setting $$\langle q|M^{-1}(Q)|q'\rangle=\sum_l R(\sigma_l(Q))\frac{\langle q|c_l(Q)\rangle\langle c_l(Q)|q'\rangle}{\sigma_l^2(Q)},\quad(13)$$

where the $|c_l(Q))$ are eigenfunctions of M(Q) with eigenvalues $\sigma_l^2(Q)$ Here $R(\sigma)$ filters the small eigenvalues, the simplest choice being a cut off whereby R is set to zero below some fixed threshold. Alternatively, Tikhonov regularization, Weiner filtering or other methods may be employed.

Example: To demonstrate the feasibility of the inversion, the reconstruction of $\alpha(r)$ has been obtained for a collection of spherical scatterers. This collection is representative of physical structures which may be imaged, such as a semiconductor; the collection presents the necessary dielectric contrast to effect direct reconstruction. The forward data was calculated by considering the scattering of evanescent waves from a homogeneous sphere including multiple scattering terms by means of a partial wave expansion. Consider a sphere of radius a centered at the point $(0,0,\alpha)$ with refractive index n, n being related to the scattering potential by the expression $n^2=1+4\pi\eta$. It may be found that $$A(k_1,k_2)=e^{ia\hat{z}\cdot(k_1-k_2)}\sum_{l=0}^{\infty}(2l+1)A_lP_l(\hat{k}_1\cdot\hat{k}_2),\quad(14)$$

where $A_l$ are the usual partial wave expansion coefficients and $P_l$ are the Legendre polynomials. Since evanescent waves are considered, the argument of the Legendre polynomials in equation (14) may exceed unity. The series may nonetheless be shown to be convergent due to the rapid decay of the $A_l$ with increasing l.

The forward data was obtained for a collection of six spheres of radius λ/20 and index of refraction n=1.1+0.2i, distributed on three planes. All scatterers are present simultaneously in the forward computation with inter-sphere scattering neglected. The set Q of transverse wavevectors was taken to be composed of all wavevectors $q_{1,2}$ corresponding to evanescent waves attainable with a prism of index n such that $|q_{1x}|\leqq nk_0$, $|q_{1y}|\leqq k_0/2$, $q_2=Q+q_1$, and the physical requirement that $k_0\leqq|q_{1,2}|\leqq nk_0$ is always imposed. When Q consists of discrete points, the integrals in equation (12) become sums. More specifically, integration over q, q' was performed on a rectangular grid with lattice spacing Δq and over Q on a rectangular grid with lattice spacing ΔQ. Regularization was achieved by setting $R(\sigma)=\Theta(\sigma-\sigma_c)$ where the cutoff $\sigma_{c=\in max(\sigma l}(Q))$ with scale factor ∈.

Figure 2:
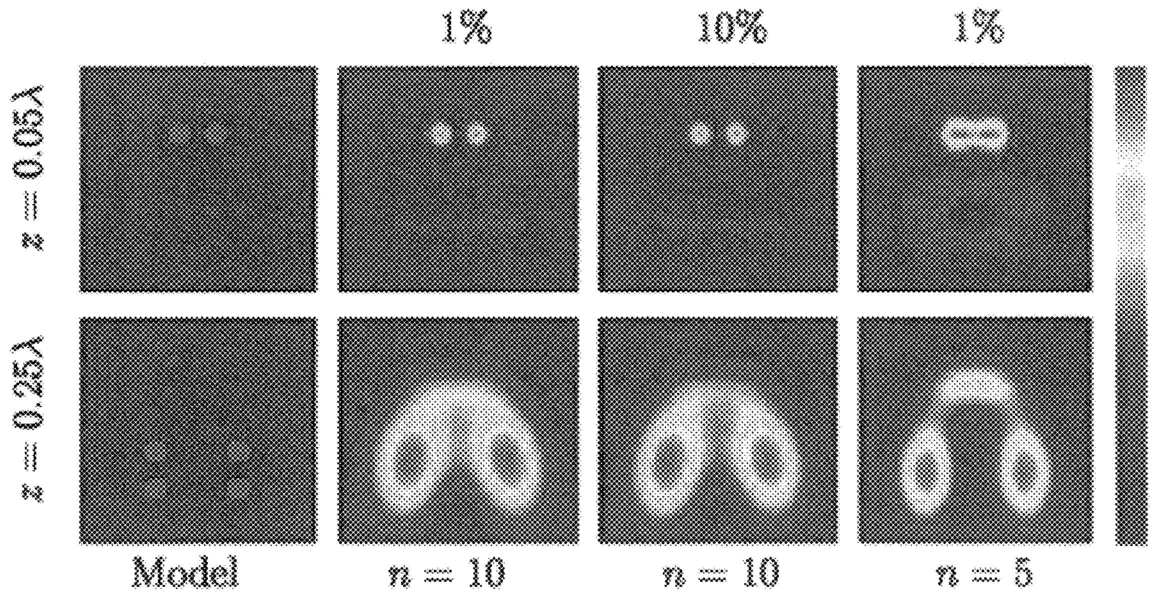
FIG. 2 depicts direct reconstruction results for an exemplary scatterer configuration.

In FIG. 2 the results are accomplished with two different prisms, one with index of refraction n=5 the other with n=10. Shown are the reconstructions obtained at depths of 0.05λ, and 0.25λ which correspond to the two separate equatorial planes of the original distribution of scatterers. The relevant parameters were taken to be $\Delta q=k_0/2$, $\Delta Q=k_0/4$ for the n=10 prism. For the n=5 case, $\Delta q=k_0/4$, $\Delta Q=k_0/8$. The regularization parameter ∈ was taken to be $\in=10^{-1}$ for the z=0.05λ layer and $\in=10^{-2}$ for the z=0.25λ layer. Complex Gaussian noise of zero mean was added to the data function at various levels as indicated.

In principle the inversion formula equation (12) provides an exact reconstruction of the scatterer when the data function is known for all possible transverse wavevectors. In practice, however, the resolution of the reconstruction is controlled by several factors including the index of the prism, the depth of the slice, and choice of regularization parameters. These effects may be understood by observing that the resolution is governed by the low pass filtering ($|Q|\leqq 2nk_0$) that is inherent in the transverse Fourier integral in equation (12) and additionally by the exponential decay of high-frequency components of the scattered field with increasing degree of evanescence. In general, with a prism of index n the transverse resolution will be on the order of λ/2n at a depth of λ/2n after which it falls off linearly. This is-seen in the n=10 case where the spheres whose edges are separated by λ/20 may be resolved in the slice at a depth of λ/20. However, the spheres in the next layer at λ/4 with the same spacing are not resolvable, but the groups of spheres which are spaced at λ/4 may be resolved. For the n=5 case the scatterers in the top layer are not well resolved, but the scatterers in the deeper layer are well resolved. That in this case the lower index prism seems to produce better images of the deeper-layer may be attributed to the fact that a fixed number of wavevectors are used, so that the reconstructions involving the lower index prism take into account a greater number of lower spatial frequency waves which probe the deeper layers.

It may be observed that the reconstruction algorithm is very robust in the presence of noise. This may be attributed to the fact that the inverse problem is over-determined. More specifically, the parameterization of the data function by $(q_1,q_2)$ is four-dimensional while the absorption is parameterized by the three-dimensional position vector r. When the data is known for a finite set of discrete points this underlying degeneracy manifests itself as a discrepancy between the number of singular functions in the regularized inversion kernel and the number of data points, the latter being greater than the former. This has the effect of performing a weighted average over groups of data points, each group being associated with a particular singular function. Since the data function is produced by taking differences between power extinction measurements, it is expected that regardless of other statistical properties of the noise it will be of zero mean. Thus the averaging process enhances the signal.

Thus, to reiterate, three-dimensional subwavelength structure of a scattering medium from power extinction measurements has been reconstructed. This process is noteworthy as follows: First, the improved resolution is made possible by the use of evanescent waves as illumination to directly probe the high spatial frequency structure of the scatterer. Second, a solution to the linearized near-field inverse scattering problem without measurement of the optical phase has been obtained. Third, the inventive technique provides an analytic solution rather than a numerical solution to the inverse problem. Finally, the technique has broad applicability, including application to the inverse scattering problem with any scalar wave using data derived from power extinction measurements.

1SYSTEM

Figure 3:
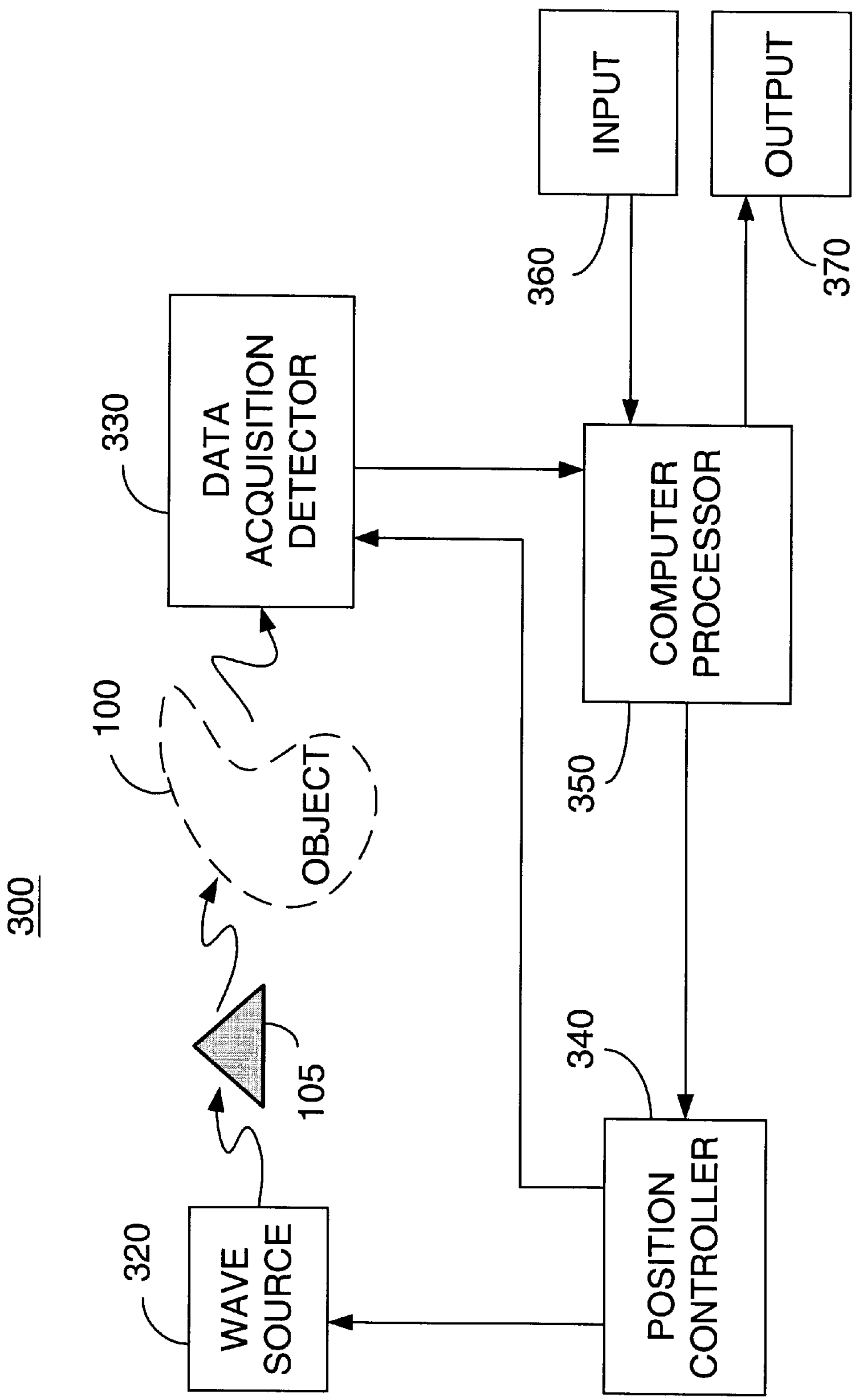
FIG. 3 is a high-level block diagram of a system for directly reconstructing the tomographic image of the scatterer.

As depicted in high-level block diagram form in FIG. 3, system 300 is a tomography system for generating an image of an scatterer/object using measurements of scattered waves emanating from an object in response to waves illuminating the object. In particular, object 100 is shown as being under investigation. System 300 is composed of: source 320 for probing the object 100 through prism 105; data acquisition detector 330 for detecting the scattering data corresponding to the scattered waves from object 100 at one or more locations proximate to object 100; position controller 340 for controlling the locations of detectors 330 and sources 320; and computer processor 350, having associated input device 360 (e.g., a keyboard) and output device 370 (e.g., a graphical display terminal). Computer processor 350 has as its inputs positional information from controller 340 and the measured scattering data from detector 330. Even though the scatterer is shown as being present in FIG. 3, actually two sets of measurements are obtained, namely, one set with the scatterer removed, and another set with the scatterer present, to provide the necessary data for image reconstruction, as detailed above.

Computer 350 stores a computer program which implements the direct reconstruction algorithm; in particular, the stored program processes the measured scattering data to produce the image of the object or object under study using a prescribed mathematical algorithm. The algorithm is, generally, determined with reference to an integral operator relating the scattering data to the forward scattering operator as expressed by integral equation (12).

FLOW DIAGRAM

Figure 4:
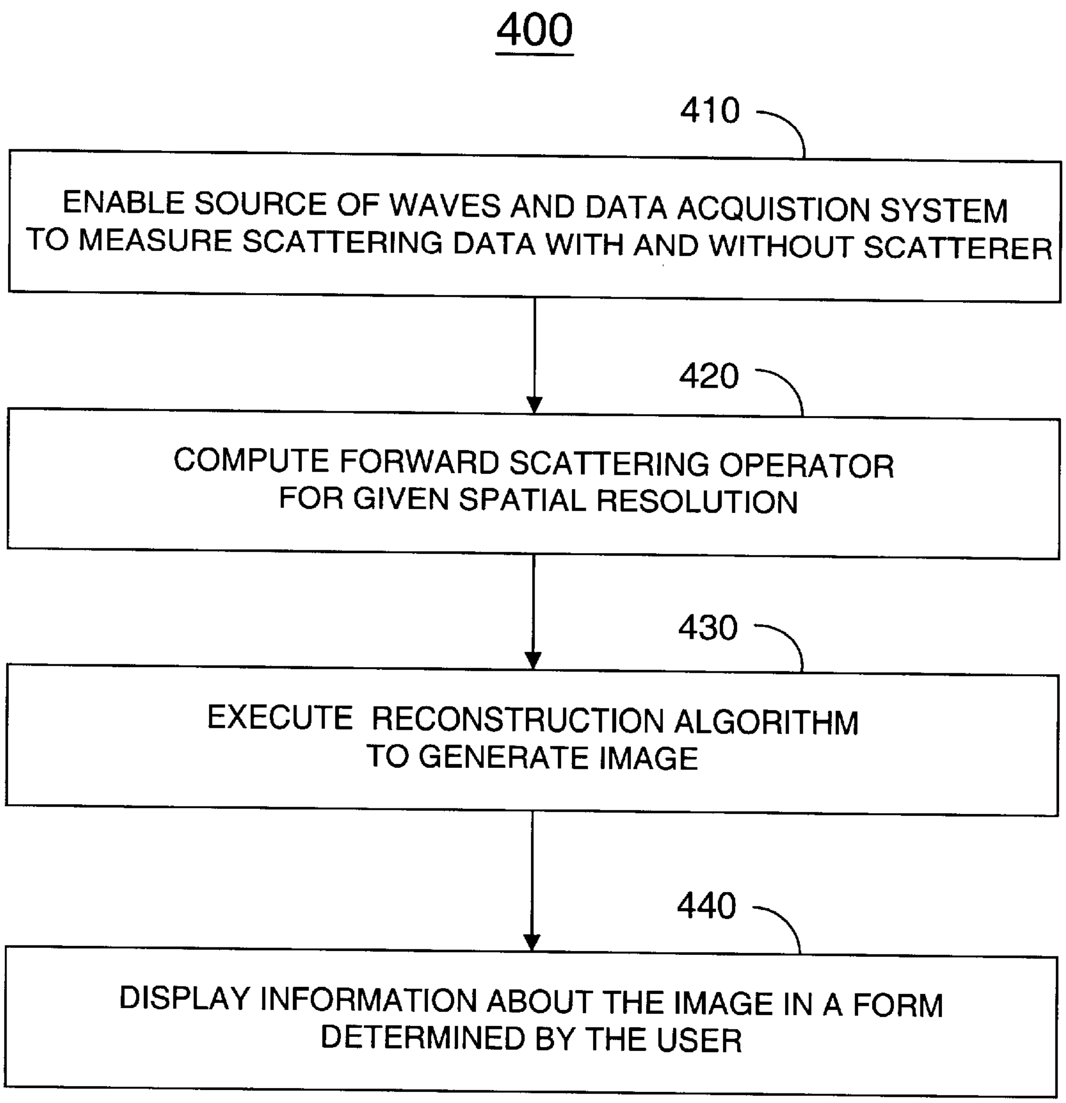
FIG. 4 is a flow diagram of the methodology for directly reconstructing the tomographic image of the scatterer.

The methodology carried out by the present invention is set forth in high-level flow diagram 400 of FIG. 4 in terms of the illustrative system embodiment shown in FIG. 3. With reference to FIG. 4, the processing effected by block 410 enables source 320 and data acquisition detector 330 so as to measure the scattering data emanating from scatterer 100 due to illuminating waves from source 320; in addition, another set of data is measured without the scatterer being present. These measurements are passed to computer processor 350 from data acquisition detector 330 via bus 331. Next, processing block 420 is invoked to compute the kernel expressed by equation (12), which may for efficiency be pre-computed and stored. In turn, processing block 430 is operated to execute the reconstruction algorithm set forth in equation (12), thereby determining the scattering potential $\alpha(r)$. Finally, as depicted by processing block 440, the reconstructed tomographic image corresponding to $\alpha(r)$ is provided to output device 370 in a form determined by the user; device 370 may be, for example, a display monitor or a more sophisticated three-dimensional display device.

Although the present invention have been shown and described in detail herein, those skilled in the art can readily devise many other varied embodiments that still incorporate these teachings. Thus, the previous description merely illustrates the principles of the invention. It will thus be appreciated that those with ordinary skill in the art will be able to devise various arrangements which, although not explicitly described or shown herein, embody principles of the invention and are included within its spirit and scope. Furthermore, all examples and conditional language recited herein are principally intended expressly to be only for pedagogical purposes to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently know equivalents as well as equivalents developed in the future, that is, any elements developed that perform the function, regardless of structure.

In addition, it will be appreciated by those with ordinary skill in the art that the block diagrams herein represent conceptual views of illustrative circuitry embodying the principles of the invention.

What is claimed is:

1. A method for generating a tomographic image of an object comprising probing the object with incident waves composed of a superposition of evanescent waves, detecting the power extinguished from the incident waves by the object, and reconstructing the tomographic image by executing a prescribed mathematical algorithm with reference to the incident waves and the extinguished power to generate the tomographic image with subwavelength resolution.

2. The method as recited in claim 1 wherein the detecting includes measuring scattering data from the object, said scattering data being related to the power exinguished from the incident waves by the object, and further related to the object by an integral operator.

3. The method as recited in claim 2 wherein the scattering data is related to a scattering potential of the object by the integral operator, and wherein the reconstructing includes reconstructing the tomographic image by executing the prescribed mathematical algorithm, determined with reference to the integral operator, on the scattering data, the prescribed mathematical algorithm further relating the scattering potential to the scattering data by another integral operator.

4. The method as recited in claim 1 wherein the probing includes illuminating a prism to generate the incident waves.

5. A method for generating a tomographic image of an object comprising illuminating the object with incident beams composed of a superposition of evanescent waves, measuring scattering data from the object wherein the scattering data is related to power exinguished from the incident beams and further related to the object by an integral operator, and reconstructing the tomographic image by executing a prescribed mathematical algorithm, determined with reference to the integral operator, on the scattering data to generate the tomographic image with subwavelength resolution.

6. The method as recited in claim 5 wherein the scattering data is related to a scattering potential of the object by the integral operator, and wherein the reconstructing includes reconstructing the tomographic image by executing the prescribed mathematical algorithm, determined with reference to the integral operator, on the scattering data, the prescribed mathematical algorithm further relating the scattering potential to the scattering data by another integral operator.

7. The method as recited in claim 5 wherein the illuminating includes illuminating a prism to generate the incident beams.

8. A system for generating a tomographic image of an object comprising a source for probing the object with incident waves composed of a superposition of evanescent waves, a detector for detecting the power extinguished from the incident waves by the object, and a processor for reconstructing the tomographic image by executing a prescribed mathematical algorithm with reference to the incident waves and the extinguished power to generate the tomographic image with subwavelength resolution.

9. The system as recited in claim 8 wherein the extinguished power determines scattering data related to a scattering potential of the object by the integral operator, and wherein the processor includes means for reconstructing the tomographic image by executing the prescribed mathematical algorithm, determined with reference to the integral operator, on the scattering data, the prescribed mathematical algorithm further relating the scattering potential to the scattering data by another integral operator.

10. A system for generating a tomographic image of an object comprising a source for illuminating the object with incident beams composed of a superposition of evanescent waves, a detector for measuring scattering data from the object wherein the scattering data is related to power exinguished from the incident beams and further related to the object by an integral operator, and a processor for reconstructing the tomographic image by executing a prescribed mathematical algorithm, determined with reference to the integral operator, on the scattering data to generate the tomographic image with subwavelength resolution.

11. The system as recited in claim 10 wherein the scattering data is related to a scattering potential of the object by the integral operator, and wherein the processor includes means for reconstructing the tomographic image by executing the prescribed mathematical algorithm, determined with reference to the integral operator, on the scattering data, the prescribed mathematical algorithm further relating the scattering potential to the scattering data by another integral operator.

* * * * *